United States Patent [19]

Layne et al.

[11] 4,094,965

[45] June 13, 1978

[54] DIAGNOSTIC AGENTS CONTAINING ALBUMIN AND METHOD FOR MAKING SAME

[75] Inventors: Warren W. Layne, Boston; Eugene L. Saklad, Sudbury, both of Mass.

[73] Assignee: New England Nuclear Corporation, Boston, Mass.

[21] Appl. No.: 783,673

[22] Filed: Apr. 1, 1977

[51] Int. Cl.² .................. A61K 29/00; A61K 43/00
[52] U.S. Cl. ................................ 424/1.5; 250/303; 252/316; 260/122; 424/1; 424/9
[58] Field of Search ............... 260/112 R, 122; 424/1, 424/1.5, 9; 252/316; 250/303

[56] References Cited

U.S. PATENT DOCUMENTS

| | | | |
|---|---|---|---|
| 3,803,299 | 4/1974 | Novel | 424/1 |
| 3,862,299 | 1/1975 | Bruno et al. | 424/1 |
| 4,024,233 | 5/1977 | Winchell et al. | 424/1 |

OTHER PUBLICATIONS

Honda et al., Journal of Nuclear Medicine, vol. 11, No. 10, Oct. 1970, pp. 580–585.
Zolle et al., International Journal of Applied Radiation and Isotopes, vol. 21, 1970, pp. 155–167.

*Primary Examiner*—Richard E. Schafer
*Assistant Examiner*—Christine M. Nucker
*Attorney, Agent, or Firm*—Dike, Bronstein, Roberts, Cushman & Pfund

[57] ABSTRACT

Diagnostic compositions comprising serum albumin which has been treated to remove fats and fatty acids with possible changes in molecular conformation, a reducing agent, preferably a stannous reducing agent, and a radionuclide, preferably technetium-99m, are highly useful in study and diagnosis of morphology and functions of animal tissues and organs, particularly in studying cardiovascular dynamics, placental imaging, cisternography, in determining blood and plasma volumes, in metabolism and turnover studies, in radioscintigraphic diagnosis of the lung and reticuloendothelial systems, e.g. pulmonary emboli, bronchogenic carcinoma, pneumonitis, emphysema, tuberculosis, pathology of liver and/or spleen manifest by changes in size or shape or pathology of adjacent structures or displacement of these organs, and other disorders.

For pulmonary and reticuloendothelial applications, the albumin is converted to particulate forms by denaturation under conditions which form aggregates of appropriate size.

29 Claims, No Drawings

DIAGNOSTIC AGENTS CONTAINING ALBUMIN AND METHOD FOR MAKING SAME

BACKGROUND OF THE INVENTION

This invention pertains to agents which are useful in medicine as aids in detecting and diagnosing disease, in the examination and evaluation of body organs, and/or for other purposes, and to diagnostic and evaluatory processes using such agents. More particularly, it is concerned with agents which can be labeled with radionuclide tracers for aid in radiological visualization of various types of tissues, including blood, body organs such as heart, liver and lungs, and other organs.

The use of tracer compounds, which emit radiation from within the body, as medical tools has long been known. Early work included the use of such materials for testing liver function and biliary patency, and for the analysis of physiological structure and function, e.g. of the kidneys.

A great deal of information about the body can be obtained by the use of tracer compositions commonly called blood pool agents. Such agents are normally radionuclide-labeled serum albumin, normally radionuclide-labeled human serum albumin for tests in humans, and human or other serum albumin, e.g. bovine serum albumin, for tests in other animals. Such reagents utilize a proteinacious carrier to which a radionuclide such as technetium-99m or iodine-131 has been attached. These agents can be used to obtain a great deal of data, including blood and plasma volume, regional cardiovascular dynamics, global cardiovascular dynamics, e.g. cardiac output, circulation times, protein turnover, placenta localization, brain tumor localization, heart imaging and liver imaging. For example, plasma volume is determined using radionuclide-labeled human serum albumin (HSA), by injecting a known volume of a known concentration of labeled HSA into the subject intravenously. The albumin is substantially confined to the plasma in the blood, and the concentration of the radionuclide-labeled albumin in the plasma is a function of the total plasma volume. By taking blood samples after brief periods, the total fixed volume can be calculated based on the total injected activity and activity measured per unit volume. It is also possible to count the whole blood to determine the whole blood volume with a reasonable degree of accuracy. See *Physician's Desk Reference for Radiology and Nuclear Medicine*, page 17 (6th ed. 1976). A blood or plasma sample is taken from the patient and counted, and the blood or plasma volume is equal to the radioactive dose originally injected divided by the activity concentration in the sample. The test is fairly reproducible and will give values for given individuals varying within about 5%. The plasma volume is obtained by withdrawing the sample and separating the plasma from the remainder of the whole blood before determining the concentration therein. Whole blood volume is determined by measuring the concentration without separation of the blood components from the sample.

Radionuclide-labeled HSA can also be used for other determinations. For example, cardiac output determinations may be indicated in patients in whom abnormalities of the heart action are detected having borderline heart failure or other myocardial abnormalities. By injecting a small bolus of radionuclide-labeled HSA, for example, and monitoring the ingress of the bolus and the egress of the radioactivity from the heart, the cardiac output can be determined. Other more efficient methods involving gated imaging are also known. Similarly, blood pool agents are useful in diagnosis of pericardial effusion, detection of shunts and other intracardiac abnormalities, differential diagnosis of midline mediastinal masses, diagnosis of ventricular or major vessel aneurysms, and evaluation of patency of major vascular pathways. Both static radiological imaging and radionuclide angiography are used. Use of these techniques to determine pericardial effusion, shunts and other intracardiac abnormalities, midline mediastinal masses, aneurysms, patency of major vascular pathways, and placental localization, particularly for the identification of placenta previa, are shown in *PDR for Radiology*, supra, at pages 44–46.

Other similar materials have been used with better advantage in other parts of the body. For example, denatured, macroaggregated HSA tagged with radionuclide, has been used to advantage in pulmonary perfusion studies in the lungs. Labeled microspheres of denatured albumin have also been used for that purpose.

Blood pool agents have also been utilized to image the liver, particularly the vascular compartment thereof. Also, microaggregates, having a particle size of less than 5μm, preferably 0.1 to 5μm, has been used to particular advantage in liver studies. Microaggregated serum albumin will be referred to as MIA, so as to distinguish between it and macroaggregated albumin (MAA).

Substantially all of the known uses of HSA have suffered from extremely difficult problems, primarily caused by the lack of stability of products containing standard human albumin, particularly at low pH. For example, preparation of stannous albumin compositions using the pH's necessary to solubilize stannous ions. Standard human serum albumin results in a product which turns cloudy and quickly precipitates out of solution. Even if it is freeze-dried (lyophilized) shortly after preparation, when it is reconstituted, turbidity forms within an hour after reconstitution. This is a serious disadvantage, particularly when the HSA is provided as part of a kit for conducting the full radiological test, since, as previously known, the HSA is so unstable that the same kit cannot be used to cover the work for a single day, i.e. the HSA clouds up and precipates are found. Yet low pH's, e.g. around 3, are necessary to ensure high uptake of the labeled HSA complex in the blood. Moreover, the effective life of some known HSA diagnostic agents is so short that they must normally be used before they can be effectively tested to ensure non-pyrogenicity and sterility thereof.

Still further problems and complications are encountered in the preparation of radioactive-labeled microaggregated and macroaggregated human serum albumin because of the difficulty in controlling the aggregation procedure so as to attain the desired particle size consistent with the intended diagnostic use of the material. Microaggregated HSA, having a particle size generally within the range of 0.1 to 5μm, is primarily used in imaging liver and spleen. Macroaggregated HSA, having a particle size greater than 5μm, preferably less than 100μm, most preferably 15 to 50μm, is an excellent agent for visualizing the lungs. These materials are selectively collected in the organs that they are used to diagnose, and they essentially collect only in those portions of the organs having sufficient blood supply, thus permitting effective visualization of areas having good and impeded blood supply. These proteinacious materials eventually dissolve, and thus do not prevent blood from reaching the areas in which they are located for significant periods.

It is, accordingly, an object of the present invention to provide a method by which serum albumin may be stabilized for use over wide pH ranges. It is a further object to provide radiological agents which are highly suited for use in vivo, giving maximal information while at the same time exposing the body to minimal radiation dosage. It is a further object of the invention to provide a composition comprising reducing agent with stabilized serum albumin, suitable for complexing or tagging with radionuclides for radioactive scanning. A still further object of the present invention is to provide radionuclide-tagged serum albumin compounds or complexes which remain soluble at low pH's and can be used to advantage for long periods for radioactive scanning. Further objects of the invention include the provision of kits suitable for carrying out the full testing procedures for radiological tests, e.g. blood volume, plasma volume, metabolism and turnover studies, analyses for pulmonary emboli, bronchogenic carcinoma, pneumonitis, pulmonary emphysema, chronic pulmonary tuberculosis, pulmonary vascular obliteration, neoplasm, pulmonary ischemia or infarction, pulmonary circulation or other disorders, brain tumor localization, cisternography, blood flow studies, cardiovascular dynamics, including cardiac output, cardiac blood volume, circulation times, protein turnover, placenta localization, brain and heart imaging, liver, spleen and bone marrow imaging, and location of growths or absesses, or for other uses.

Further objects and advantages of the present invention will be readily apparent to the skilled in the art from a consideration of the present disclosure or from practice of the invention disclosed herein.

SUMMARY OF THE INVENTION

It has now been found that serum albumin can be stabilized to give clear solutions for extended periods of time over wide pH ranges by removal of the fats and fatty acids contained in normal serum albumin.

One form of normal human serum albumin, USP, for example, is supplied as a 25% solution of human albumin in an aqueous diluent buffered with sodium carbonate or other buffering medium. Typically, the product may be stabilized with small amounts, e.g. about 0.02 M, sodium carpylate, and small amounts, e.g. 0.02 M, of acetyltryptophane. For normal human serum albumin, not less than 96% of its total protein is albumin. However, substantial amounts of lipids, i.e. fats and fatty acids, are contained in normal serum albumin. From experience in the field, commercially available serum albumin generally contains well over 3 moles of lipid per mole of albumin, based on a molecular weight of albumin of 69,000.

In accordance with the present invention, the amount of lipid contained in serum albumin is reduced to less than 3 moles of lipid per mole of albumin, preferably less than 2 moles of lipid per mole of albumin, and more preferably less than about 0.1 mole of lipid per mole of protein. The concentration of lipids in the albumin should be reduced to a sufficient level that the product of admixture of the albumin, the reducing agent and the radionuclide does not become cloudy for at least one hour, more preferably four hours, most preferably eight hours, at a pH of about 3 or less.

A variety of methods may be used to separate the lipids from the serum albumin. The most preferred method is treatment of albumin solutions with charcoal at lower pH's, e.g. in the manner disclosed in R. F. Chen, "Removal of Fatty Acids from Serum Albumin by Charcoal Treatment," *J. Biol. Chem.* 212:173 (1967), incorporated herein by reference. In accordance with that method, the commercial HSA solution is acidified to a pH below 7, preferably 0 to 5, more preferably 1 to 2.5 (a pH of about 1.5 is acceptable), and the acidified solution is treated with charcoal. The pH should be sufficiently low to separate the fatty acids but not so low as to hydrolyze the protein. The charcoal is preferably added in the amount of 0.1 grams per gram of albumin to 10 grams of charcoal per gram of albumin. A preferred range for addition is about 0.2 gram charcoal per gram of albumin to about 1.5 grams per gram of albumin. Most preferably the delipidation is achieved at low temperatures, to avoid or minimize the possiblity of adverse chemical reaction of the protein in an acid medium. The temperature should be generally be from $-2°$ C to $+30°$ C, preferably between about $0°$ C and $10°$ C. The solution can be contacted with the charcoal for a period of between a few minutes and 3 or 4 hours, depending upon the pH, the temperature, and the concentration of albumin. Normally a period of about 1 hour is sufficient time for contact. It is preferred to stir the mixture during the contact period, or in any other appropriate fashion, to maintain the maximum contact between the protein and the charcoal. The concentration of the albumin in the solution being contacted can generally range from about 1% to 25%, preferably about 3% to 10%, more preferably about 4% to 6% by weight. A wide variety of commercially available charcoals are usable with the process. Suitable materials include Darco M, sold by Atlas Chemical Industries, Norit charcoals, e.g. Norit A, sold by Caswell-Massey Co., and Nuchar activated carbon, sold by West Virginia Pulp and Paper Co. Other suitable carbons are well known and will be readily apparent to those skilled in the art. After maintaining contact for the period of time discussed above, the carbon and sorbed lipids are separated from the remaining albumin solution. This may be accomplished by centrifugation, filtering, sedimentation, or other methods readily apparent to the skilled in the art. The preferred method of separation is by filtration, particularly submicron filtration, primarily because it renders an albumin solution which is not only carbon free, but is also sterile, and therefore can be used directly in the testing processes. Some other materials, e.g. preservatives and a small amount of albumin, may also be absorbed or adsorbed by the carbon particles, but surprisingly small amounts of albumin are lost in the defatting or delipidation process as described.

Another method of defatting the albumin solution to be used is by the acid precipitation method, e.g. as described by Williams et al, *J. Am. Chem. Soc.* 80:1789 (1958), and Foster et al, *J. Biol. Chem.* 240:2494-2502 (1965), both incorporated herein by reference. Thus concentrated albumin solutions can be acidified to a pH of, e.g., 2.9 and maintained at that pH for 2 to 3 days, during which time the lipids present form a separate phase which can be removed, e.g. by centrifugation. Or concentrated albumin solutions can be acidified to lower pH's, e.g. a pH of 1.0 to 2.0, at which time lipid phase separation occurs more rapidly, which permits somewhat more rapid separation of the lipid phase from the albumin solution.

Other methods of delipidizing the albumin may also be used, including contact with absorptive or adsorptive columns, see, e.g., Scheider et al, *Biochim. Biophys. Acta* 221:376 (1970); solvent extraction, see, e.g., Goodman, *Science* 125:1296 (1957); biological extraction, see, e.g., Scheider et al, *Biophys. J.* 16:417-31 (1976); and other methods known in the art. While it is not presently clear, it is possible that acidification may work changes in the molecular structure of the albumin, which changes would be avoided by the biological extraction techniques.

After removal of the lipid impurities, the defatted albumin is preferably combined with a reducing agent to form a material which is quite easily labeled with radionuclide. Preferred reducing agents are sources of ferrous ions, e.g. ferrous ascorbate, and sources of stannous ions, e.g. stannous chloride, with the stannous ions being most preferred. While not wishing to be bound by theory, it is believed that when the radionuclide, reducing agent, and protein are co-present in solution, a reaction takes place by which the radionuclide is reduced and forms some kind of combination with the protein, which is believed to be a radionuclide-reducing agent-protein complex, preferably a technetium-tin-albumin complex. In the preferred embodiment, the albumin and reducing agent are premixed in solution, the solution is freeze-dried, and is used as part of the kit. When it comes time to use the kit, the reducing agent-albumin is reconstituted with a source of the radionuclide, e.g. pertechnetate ions, and the labeled albumin is formed. It is not known precisely what occurs between the defatted albumin and the reducing agent, in the absence of technetium, at the time it is mixed and prior to the lyophilization thereof. It may be that the reducing agent is sorbed by the rather large (M.W. 69,000) albumin molecules and maintained in that state during lyophilization until combination with technetium ion in solution is effected.

The source of technetium should be water soluble, with preferred sources being alkali and alkaline earth metal pertechnetates. The technetium is preferably obtained in the form of fresh sodium pertechnetate from a sterile NEN $^{99m}$Tc Generator. Any other source of pharmacologically acceptable $^{99m}$Tc can be used, and a number of $^{99m}$Tc generators are available.

The maximum amount of reducing agent which can be used is the amount beyond which precipitation of the reducing agent occurs, and the minimum amount required is that amount necessary to bind a sufficient amount of $^{99m}$Tc to the protein to achieve significant plasma, tissue, or organ uptake. These amounts can be readily determined for particular technetium-reducing agent-albumin mixtures by routine experimentation. Very small amounts of reducing agent are effective for this purpose, but because such agents are usually easily oxidized, compositions using the extremely small amounts are likely to lose this effectiveness over a period of time after handling or during use. Thus, as a minimum, the amount of reducing agent used should be calculated to be sufficient to supply at least 0.1μg of reducing agent per ml of the diagnostic agent to be injected. As the amount of reducing agent is increased, there appears to be a point for any given combination of particular reducing agent and albumin, beyond which binding effectiveness to the protein no longer increases, and, in fact, may decrease, upon further addition of reducing agent. Some level of such binding effectiveness appears to be achieved for even very high levels of reducing agent. Advantage can sometimes be taken of the natural attrition of reducing agent through oxidation during handling or storage, by providing compositions containing more than the optimum amount of reducing agent, which in effect will be reduced to the optimum amount by that attrition prior to use. Normally, the albumin will be in large excess of the reducing agent. Preferably the reducing agent should be present in an amount of about 0.0005% to 100%, more preferably from 0.005% to 1% of the albumin.

Sufficient radionuclide, preferably technetium-99m, should be present to give easy detection in the body. The amount necessary appears to depend essentially completely on the level of radioactivity desired, since if the proper amounts and ratios of reducing agent and albumin are present, the vast majority of technetium, as much as 90–95% or more, is bound to the albumin.

In the presently preferred system, a sterile, nonpyrogenic lyophilized mixture of about 0.1 milligrams of stannous chloride dihydrate reducing agent and about 25 milligrams of defatted human serum albumin are provided in a sterile vial, which is preferably mixed with 3 to 7 ml of the output of an NEN $^{99m}$Tc generator, shortly before use.

The diagnostic compositions of the invention may also contain additional pharmacologically acceptable ingredients which do not interfere with there diagnostic functions. For example, the eluate obtained from standard $^{99m}$Tc generators contains sodium salts, or saline solutions may be used to dilute the ingredients to the proper concentration prior to lyophilization or to dilute radioactive diagnostic compositions to the proper level for administration. Also, non-interfering acids and bases, such as hydrochloric acid or sodium hydroxide, may be used to adjust the pH to the desired level, e.g. prior to lyophilization of the albumin/stannous material. Preferably the lyophilized reducing agent/albumin admixture also contains small amounts of non-ionic surface active agents, preferably the normally solid non-ionic surface active agents, e.g. the ethylene oxide/propylene oxide/propylene glycol condensates sold under the mark Pluronic, particularly Pluronic F68, by BASF Wyandotte, which facilitates reconstitution of the lyophilized admixture. Aseptic techniques and sterile, non-pyrogenic ingredients and containers should be used at all steps, such procedures being standard to those skilled in the art. In order to prevent oxidation of the stannous ions other than in formation of the complex, care should be taken to exclude oxidizing agents from the starting materials. For this reason, sources of technetium-99m containing significant amounts of oxidants should not be used. Oxygen should also be excluded, as by purging the various containers used in preparation and storage of the ingredients or intermediate products, with an inert gas, such as nitrogen, for a sufficient length of time. However, it is not essential, although highly preferred, to use an inert gas flush system.

After mixing, the solution containing the reducing agent and the defatted albumin can be sterilized if necessary by standard procedures, as by passing them through a biological filter of about 0.22 micron pore size, preferably under a nitrogen atmosphere. Thereafter portions of the sterile solutions are poured into individual sterile and non-pyrogenic storage glass vials under a nitrogen atmosphere. They are preferably then lyophilized by conventional freeze-drying techniques under aseptic conditions to remove water. This provides a solid stannous-albumin complex or mixture of some sort, which aids in shipping and storage and is more stable than the complex in solution. The vials can be sealed and stored until needed to form the fresh $^{99m}$Tc-stannous-albumin agent at the place of use.

While it is preferred that the stannous chloride and defatted albumin be mixed together prior to admixture with technetium, the order of the mixture can also be technetium plus defatted albumin followed by admixture of stannous chloride.

In accordance with the present invention, the delipidized albumin can also be used to advantage in diagnostic agents containing denatured (aggregated) albumin, including both agents incorporating microaggregated albumin and those incorporating macroaggregated albumin. The microaggregates or macroaggregates may be made from the delipidized albumin, e.g. by heat treating at 55°-100° C at a pH of between 4-10, as will be understood by the skilled in the art. In making MAA, such treatment can be followed by a further heat treatment at about the same temperature, after adjusting the pH to approximately the isoelectric point of albumin, e.g. a pH of about 5-5.5. Preferably the MAA is made by a single heat treating step at about 55°-75° C, for 10 minutes to 2 hours or more, until the desired particle size and firmness reached to give proper biological clearance in use. It has been found that the use of delipidized HSA actually improves the yield of MAA produced substantially, as compared with MAA prepared from untreated HSA.

Both MIA and MAA materials may advantageously contain 10-75% of undenatured albumin (as well as other materials) which is known to aid in providing a matrix for effective lyophilization and reconstruction. In accordance with the present invention, the undenatured albumin used in such MIA and MAA materials can also be delipidized albumin.

In use, the technetium-99m-stannous-defatted albumin complex or mixture is injected aseptically into the blood stream. The preferred dosages are between about 1 to 400μCi per kilogram of body weight, depending upon the nature of the tests to be performed, and the nature of the subject on which the test is to be performed. For example, for static blood pool imaging in normal adults (body weight about 70 kg) 3 to 5mCi of technetium labeled albumin may be administered intravenously and imaging started shortly thereafter. For radionuclide angiocardiography, gated cardiac studies, and cardiac ventriculography, the dose may generally be 10 to 20mCi administered in a small bolus (1 to 2 ml) intravenously. For placenta localization, the recommended intravenous dose is about 1mCi. For blood volume determinations, an intravenous dose of about 0.2-1mCi can be sufficient. Pediatric doses are generally less than adult doses, and it is generally considered desirable not to exceed 100 to 200mCi per kilogram of body weight for pediatric subjects. However, such heightened safety considerations need not be controlling in animal studies, e.g., with rats, mice, dogs, etc. The above dosages are exemplary, and higher or lower amounts may be used in certain circumstances, although greater dosages increase patient radiation exposure.

Generally the study or test may be commenced immediately after administration either by sequential visualization devices, such as scintillation cameras, or by probes of various known types. For cardiac studies and the like, it may be desirable to be monitoring heart radiation essentially immediately after introduction of the bolus into the patient. On the other hand, for some studies requiring blood or other equalization, a waiting period may be found desirable, as will be understood by the skilled in the art.

The invention will be further clarified with reference to the following illustrative embodiments, which are intended to be purely exemplary and not to be construed in any limiting sense.

EXAMPLE I

Delipidation of Albumin-Carbon Method

Cool 60 ml of a commercial 25% solution of normal human serum albumin (Cutter) to 0°-10° C in a clean, non-pyrogenic beaker. Place the beaker in an ice pack in order to maintain temperature. Acidify the HSA solution to a pH of about 2.2 to 2.5, by adding 319 ml of 0.1 N HCL, also cooled to 0°-10° C. This addition should be made with stirring. Add 15.2 grams of Nuchar-C-190-N carbon to the beaker and stir for 1 hour at 0°-10° C. Remove the carbon/lipid by filtering the batch aseptically through a clean, non-pyrogenic filter into a clean, non-pyrogenic container. Preferably, this product should be further sterilized by filtration through at least one sterilizing filter or membrane, e.g., a Millipore 0.22μm filter. This procedure will yield approximately 400 ml of sterile, non-pyrogenic, delipidized HSA solution.

EXAMPLE II

Delipidation of HSA-Acidification Method

Acidify 10 ml of 25% by weight normal human serum albumin (Cutter) with 87 ml of 0.1 N HCl to a final pH of about 1.5. Within about 10 minutes after acid addition, sterile filter the entire solution into two sterile 50 ml vials through an 0.22μm Millipore filter, and store the resulting vials at 0°-10° C for about 16 hours. These solutions will have become quite hazy with settled white particulates. Accordingly, they should be refiltered through 0.22μm sterile filters to remove the precipitated acid. It may be necessary to use a number of filters in this procedure, since the small pore filters are clogged easily, sometimes with 8 to 10 milliliters of this solution. The filtrate from the second filtration step should be clear, and filtrate obtained in this manner has remained clear for several weeks, until the supply was exhausted. The resulting solution contains about 24.5 milligrams of total protein per milliliter, and about 1.7 moles of fatty acid per mole of HSA.

EXAMPLE III

Preparation of Freeze-Dried Kits.

Dissolve 1 gram of stannous chloride dihydrate in 1 ml of concentrated hydrochloric acid. Dilute to 10 ml with deoxygenated saline. Remove 1 milliliter of the resulting solution and dilute that 1 ml to 10 ml with deoxygenated saline. In a separate flask, dissolve 2 grams of Pluronic F68 surface active agent in 100 ml of deoxygenated saline.

From an analysis of the delipidized HSA produced by the carbon or acidification method determine what volume of the delipidized HSA contains 25 grams of albumin. Add the entire 10 milliliters of the second dilution of stannous chloride to that volume of delipidized HSA which contains 25 grams of albumin. Also add the entire contents of Pluronic F68 solution to the mixture of the stannous chloride and the delipidized HSA. This solution should be maintained under an inert gas such as nitrogen. Bring the volume of this mixture to 1 liter with deoxygenated saline and filter the mixture through a sterile 0.22μm membrane. Thereafter, 1 milliliter samples are dispensed in vials and are freeze-dried in accordance with standard commercial techniques. The vials are maintained under an atmosphere of nitrogen after freeze-drying.

EXAMPLE IV

Preparation of Labeled Albumin Blood Pool Agent.

The lyophilized vials prepared in accordance with Example III will each contain about 25 mg of normal human serum albumin, 0.1 mg of stannous chloride dihydrate and 2 mg of Pluronic F68, all in lyophilized form. Aseptically injecting 2-7 ml of the sterile eluate from an NEN $^{99m}$Tc generator, which is a solution of sodium pertechnetate Tc-99m in isotonic saline without a bacteriostat reconstitutes the lyophilized material and generates the technetium-99m-tin-albumin. The injection should take place behind a radiation shield, since the eluate from the $^{99m}$Tc generator, and the technetium-99m-tin-albumin complex or mixture are radioactive. The vial is swirled to dissolve the lyophilized solid completely. When all of the material is in solution, the material is ready to use.

The compositions were tested by reconstituting lyophilized albumin-tin prepared in the above manner with 5 ml of an eluate from an NEN $^{99m}$Tc generator. 0.25 ml of this solution was injected into the tail vein of adult rats weighing 200-300 grams. Injections Injections were made approximately one hour after reconstitution. The rats were sacrificed about 45 minutes after injection and the blood collected. On the assumption that the normal blood pool accounts for 5% of the rat body weight, (see Sharpe et al, Proc. Soc. Exp. Biol. 74:681) (1950) the blood uptake values for diagnostic agent prepared from albumin which was delipidized by the charcoal method in accordance with Example I was 36.5 plus or minus 3.5% (average, 30 animals, 10 vials). The blood value measured in rats using the composition made from albumin delipidized in accordance with the acid precipitation method of Example II was comparable, at 36.7 plus or minus 3% (1 vial, 3 animals).

EXAMPLE V

Use of Delipidized HSA for Preparation of Stannous Macroaggregated Albumin.

To 463 ml of low oxygen water was added with mixing 44 ml of an an aqueous solution of delipidized HSA (38 mg/ml, pH 2.5), 0.17 grams of stannous chloride dissolved in 1.25 ml of 12 Normal hydrochloric acid, 7.9 grams of sodium acetate, and 1.33 ml of an aqueous solution of Polysorbate 80 U.S.P. (50 mg/ml). After complete dissolution of the sodium acetate, the solution was heated to 63°-65° C and held with mixing in that temperature range for 30 minutes. The aggregates thus formed of stannous denatured albumin were allowed to settle. Removal of the supernant and resuspension in low oxygen water two times gave a 92% yield of macroaggregates (average particle size 30 to 35 μm) relative to the albumin in the solution before aggregation. (The yield from unpurified normal human serum albumin is characteristically 55 to 70,%). A $^{99m}$Tc-labeled preparation of these aggregates showed activity distribution to rat lungs of about 89% of the injected dose 15 minutes after injection, dropping to about 2% at 24 hours. These results are highly desirable characteristics of an agent for imaging lung perfusion.

While particular embodiments of the present invention have been described herein, they are intended to be exemplary only, with the true scope and spirit of the invention being indicated in the specification and the following claims

We claim:

1. A material for labeling with a radionuclide (for radioactive testing) comprising the product of admixture of a reducing agent and serum albumin from which lipids have been removed.

2. The material of claim 1, wherein the amount of lipids is less than about 2 moles per mole of albumin.

3. The material of claim 1, wherein the amount of fatty acid is less than about 0.1 mole per mole of albumin.

4. The material of claim 1, wherein the stannous is present in amounts of about 0.0005% to 10% by weight of the albumin.

5. The material of claim 1, wherein the albumin is macro-aggregated albumin.

6. The material of claim 1, wherein the albumin is micro-aggregated albumin.

7. The method of making a material for complexing with a radionuclide for radioactive scanning, comprising removing lipids from serum albumin to produce defatted albumin and mixing the defatted albumin with a source of stannous ions at a pH below 7.

8. The method according to claim 7 wherein the lipids are removed from the normal human serum albumin by contacting the normal human serum albumin with carbon, and separating the carbon and sorbed fatty acids from the defatted albumin.

9. The method of claim 7 further comprising forming aggregates of defatted albumin having a particle size of about 0.1 to 100 μm.

10. The method of claim 9 where the particle size of the aggregates are about 15 to 50 μm.

11. A diagnostic agent for use in radiological testing, comprising the product of admixture of a source of radionuclide ions, a reducing agent, and a defatted albumin, said defatted albumin being sufficiently purified that an aqueous solution of said agent does not become cloudy for at least one hour at a pH of 4 or below.

12. The agent of claim 11, wherein the radionuclide is technetium.

13. The agent of claim 11, wherein the reducing agent is a stannous reducing agent.

14. The agent of claim 13, wherein the stannous ions are present in an amount of 0.0005% to 0.5% of the weight of the defatted albumin.

15. The agent of claim 14 wherein the defatted albumin is denatured defatted albumin, having a particle size of about 0.1 to 100 μm.

16. The agent of claim 15 wherein the denatured defatted albumin is macroaggregated albumin having a particle size of about 15-50 μm.

17. A method of making radioactive diagnostic agent suitable for use in radiological scanning, comprising delipidizing normal human serum albumin, and mixing the delipidized normal human serum albumin with a source of radionuclide and a source of reducing agent.

18. The method of claim 17, wherein the radionuclide is technetium-99m.

19. The method of claim 17, wherein the reducing agent is stannous.

20. A kit for forming a radioactive diagnostic composition comprising a reducing agent and delipidized serum albumin, packaged in a sealed, sterile, non-pyrogenic container.

21. The kit of claim 20 wherein said reducing agent and said delipidized serum albumin are in the form of a freeze-dried solid.

22. The kit of claim 20 wherein the reducing agent is stannous.

23. A method of concentrating technetium-99m in vivo in a target tissue of a mammal comprising intravenously administering to the mammal a radioactive composition comprising a mixture of technetium-99m, a reducing agent and delipidized serum albumin.

24. The method of claim 23, wherein said composition contains sufficient technetium-99m to provide radioactivity in the amount of from about 1 to 400μci per kilogram of body weight.

25. The method of claim 23, wherein the reducing agent comprises a stannous reducing agent.

26. A method of preparing a radioactive diagnostic agent, comprising forming a mixture of a reducing agent and delipidized serum albumin, and combining technetium-99m with said mixture.

27. The method of claim 26, wherein said mixture is lyophilized prior to being combined with technetium-99m.

28. The method of claim 17, wherein the albumin is micro-aggregated albumin.

29. The method of claim 17 wherein the albumin is macro-aggregated albumin.

* * * * *

UNITED STATES PATENT AND TRADEMARK OFFICE
CERTIFICATE OF CORRECTION

PATENT NO. : 4,094,965

DATED : June 13, 1978

INVENTOR(S) : Warren W. Layne and Eugene L. Saklad

It is certified that error appears in the above-identified patent and that said Letters Patent are hereby corrected as shown below:

Col. 1, line 14, change "and" (first occurrence) to ---,---.

Col. 2, line 25, change "has" to ---have---.

Col. 2, line 27, change "MIA" to ---µAA---.

Col. 2, line 37, change "cloudly" to ---cloudy---.

Col. 2, line 45, change "precipates" to ---precipitates---.

Col. 2, line 47, change "uptake" to ---retention---.

Col. 3, line 49, change "carpylate" to ---caprylate---.

Col. 4, line 21, delete "be" (first occurrence).

UNITED STATES PATENT AND TRADEMARK OFFICE
CERTIFICATE OF CORRECTION

PATENT NO. : 4,094,965

DATED : June 13, 1978

INVENTOR(S) : Warren W. Layne and Eugene L. Saklad

It is certified that error appears in the above-identified patent and that said Letters Patent are hereby corrected as shown below:

Col. 6, line 27, change "there" to ---their---.

Col. 6, line 38, change "admisture" to ---admixture---.

Col. 6, line 64, change "poured" to ---dispensed---.

Col. 6, line 66, delete "under a nitrogen atmosphere".

Col. 7, line 18, change second "-" to ---and---.

Col. 7, line 26, insert ---is--- between "firmness" and "reached".

Col. 7, lines 31 and 36, change "MIA" to ---μAA---.

Col. 7, line 41, change "to" to ---and---.

UNITED STATES PATENT AND TRADEMARK OFFICE
CERTIFICATE OF CORRECTION

PATENT NO. : 4,094,965
DATED : June 13, 1978
INVENTOR(S) : Warren W. Layne and Eugene L. Saklad It is certified that error appears in the above-identified patent and that said Letters Patent are hereby corrected as shown below:

Col. 7, line 56, change "200mCi" to ---200µCi---.

Col. 8, line 41, change "acid" to ---fatty acids---.

Col. 9, line 7, change "maintained" to ---sealed---.

Col. 9, line 19, insert ---,--- after "bacteriostat".

Col. 9, between lines 30 and 31, before "adult rats" insert ---each of several---.

Col. 9, line 34, insert from each was--- between "blood" and "collected".

Col. 9, line 37, change "uptake values for" to ---retention for the---.

UNITED STATES PATENT AND TRADEMARK OFFICE
CERTIFICATE OF CORRECTION

PATENT NO. : 4,094,965
DATED : June 13, 1978
INVENTOR(S) : Warren W. Layne and Eugene L. Saklad It is certified that error appears in the above-identified patent and that said Letters Patent are hereby corrected as shown below:

Col. 9, line 40, insert ---of the injected radioactivity--- between "%" and "(".

Col. 9, line 51, delete "an" (first occurrence).

Col. 9, line 60, change "supernant and resuspension in" to ---supernatant and resuspension of the sediment in---.

Col. 9, line 65, delete ",".

Col. 9, line 66, change "aggreates" to ---aggregates---.

Col. 10, line 60, change "making radioactive" to ---making a radioactive---.

Signed and Sealed this

Twenty-seventh Day of February 1979

[SEAL]

Attest:

RUTH C. MASON
Attesting Officer

DONALD W. BANNER
Commissioner of Patents and Trademarks